(12) United States Patent
Schroeder et al.

(10) Patent No.: US 11,504,718 B2
(45) Date of Patent: Nov. 22, 2022

(54) INCUBATION TROUGH AND INCUBATION TRAY WITH A PLURALITY OF INCUBATION TROUGHS

(71) Applicant: EUROIMMUN Medizinische Labordiagnostika AG, Luebeck (DE)

(72) Inventors: Dieter Schroeder, Stockelsdorf (DE); Patrick Auer, Stepenitztal (DE); Alf Weimann, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 916 days.

(21) Appl. No.: 16/298,322

(22) Filed: Mar. 11, 2019

(65) Prior Publication Data
US 2019/0275524 A1    Sep. 12, 2019

(30) Foreign Application Priority Data
Mar. 12, 2018   (EP) .................................... 18161240

(51) Int. Cl.
*B01L 3/00*      (2006.01)
*G01N 33/543*    (2006.01)
(Continued)

(52) U.S. Cl.
CPC ............. *B01L 3/52* (2013.01); *B01L 3/50855* (2013.01); *B01L 9/52* (2013.01); *G01N 33/5302* (2013.01);
(Continued)

(58) Field of Classification Search
CPC ......... G01N 33/54386; G01N 33/5304; G01N 2035/00108; G01N 33/54387;
(Continued)

(56) References Cited

U.S. PATENT DOCUMENTS 8,107,066 B2 *   1/2012   Dirla ....................... B29C 51/30
                                                    356/244
2007/0237687 A1  10/2007  Sleeper
(Continued)

FOREIGN PATENT DOCUMENTS

CN    103091482       5/2013
CN    205199533 U     5/2016
(Continued)

OTHER PUBLICATIONS

European Search Report dated May 25, 2018 in European Application No. 18161240.9, with English translation (10 pages).
(Continued)

*Primary Examiner* — Christopher L Chin
(74) *Attorney, Agent, or Firm* — Grüneberg and Myers, PLLC

(57) ABSTRACT

An elongated incubation trough has an indentation open toward a top end as well as a bottom. The indentation has a first receiving area to receive an elongated test strip as well as a second receiving area to receive an end section of a fluid line. The second receiving area is in fluidic communication with the first receiving area. A maximum width of the second receiving area at bottom height is greater than a maximum width of the first receiving area at bottom height.

14 Claims, 8 Drawing Sheets

(51) Int. Cl.
*B01L 9/00* (2006.01)
*G01N 33/53* (2006.01)
*G01N 35/00* (2006.01)

(52) U.S. Cl.
CPC . *G01N 33/54366* (2013.01); *G01N 33/54386* (2013.01); *B01L 2200/026* (2013.01); *B01L 2200/16* (2013.01); *B01L 2300/0663* (2013.01); *B01L 2300/0825* (2013.01); *B01L 2300/0848* (2013.01); *G01N 2035/00108* (2013.01); *G01N 2035/00356* (2013.01)

(58) Field of Classification Search
CPC ....... G01N 33/54388; G01N 33/54389; G01N 33/54391; G01N 33/543; G01N 33/54306; G01N 33/558; G01N 33/5302; G01N 33/54366; G01N 2035/00356; B01L 2300/0825; B01L 3/52; B01L 3/50855; B01L 3/5085; B01L 9/52; B01L 2200/026; B01L 2200/16; B01L 2300/0663; B01L 2300/0848; B01L 2300/0858; B01L 2300/0861; B01L 3/00; B01L 3/50
USPC ....... 422/400, 401, 420, 421, 425, 426, 430, 422/551, 552; 435/287.7, 287.9, 288.3, 435/970, 975, 805, 810; 436/169, 170, 436/514, 518, 530, 808, 809, 810
See application file for complete search history.

(56) References Cited

U.S. PATENT DOCUMENTS

| | | | | |
|---|---|---|---|---|
| 2015/0301035 | A1* | 10/2015 | Meyer | G01N 33/56911 |
| | | | | 422/417 |
| 2016/0097724 | A1* | 4/2016 | Meyer | G01N 21/8483 |
| | | | | 422/69 |
| 2017/0225170 | A1* | 8/2017 | Wu | B01L 9/50 |

FOREIGN PATENT DOCUMENTS

| | | |
|---|---|---|
| DE | 20 2012 004 404 U1 | 8/2012 |
| EP | 0 720 020 | 7/1996 |
| EP | 3 025 779 | 6/2016 |
| EP | 3 025 780 | 6/2016 |
| EP | 3 085 446 | 10/2016 |
| EP | 3 196 209 | 7/2017 |
| EP | 3 244 212 | 11/2017 |
| EP | 2 295 898 | 8/2018 |
| EP | 3 156 798 | 12/2018 |
| KR | 10-2010-0073241 | 7/2010 |
| TW | M486769 U | 9/2014 |

OTHER PUBLICATIONS

Chinese Office Action dated Jun. 24, 2022, in Chinese Application No. 201910182222.2, 4 pages.

* cited by examiner

Fig. 1
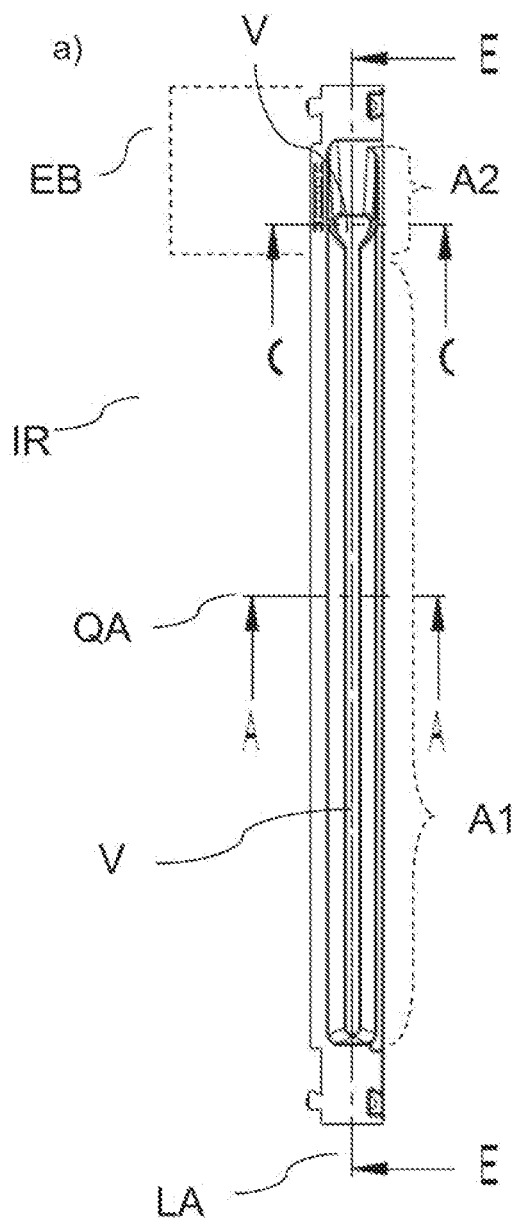
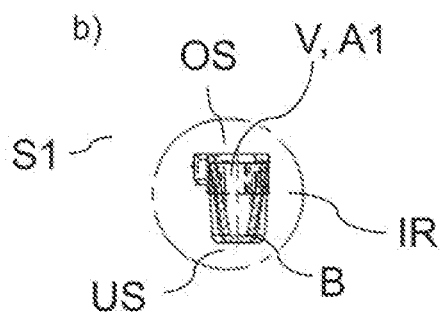
Cross section A-A
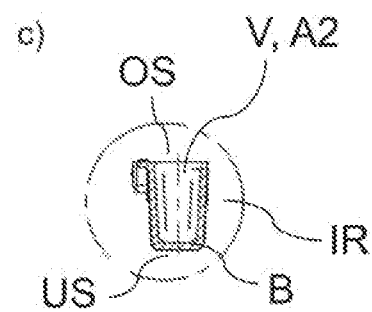
Cross section C-C

Cross section E-E

INCUBATION TROUGH AND INCUBATION TRAY WITH A PLURALITY OF INCUBATION TROUGHS

CROSS-REFERENCE TO RELATED APPLICATIONS

The present application claims priority to European patent application EP 18 161 240.9 filed Mar. 12, 2018, which is incorporated by reference in its entirety.

BACKGROUND OF THE INVENTION

Field of the Invention

The invention relates to an elongated incubation trough, having an indentation open toward a top end of the incubation trough, extending along a longitudinal direction of the incubation trough. Moreover, the incubation trough has a bottom, which bounds the indentation toward a lower end of the incubation trough. The indentation has a first receiving area to receive an elongated test strip. In a preferred receiving of the test strip in the first receiving area, the test strip faces toward the bottom with its back side and is coated with at least one analytical reagent on its front side. According to the invention, the indentation moreover has a second receiving area, which is designed to receive an end section of a fluid line, the second receiving area being in fluidic communication with the first receiving area. According to the invention, it is provided that a width of the second receiving area at bottom height is greater than a width of the first receiving area at bottom height.

Description of Related Art

In the field of medical laboratory diagnostics, various test systems are known with which patient samples can be investigated for the presence of specific antibodies. With such tests, it is possible to draw conclusions as to the presence of diseases occurring together with such specific antibodies. The disease may occur as a result of the formation of auto-antibodies or the antibodies are formed as a reaction to the disease, for example as a reaction to the advent of pathogenic viruses. Such diseases include infections, inflammatory illnesses such as rheumatoid diseases, metabolic diseases such as diabetes and neurological ailments.

These strips are also referred to as test strips, which are usually inserted into incubation troughs for incubation with liquid reagents, so that the test strip comes into contact with the reagent liquid in the incubation trough for a certain period of time.

Such a test strip usually has a longitudinal extent as well as a front side and a back side. The test strip usually lies in the incubation trough such that it lies by its back side against the bottom of the incubation trough or faces the bottom, and its front side faces toward the top end of the incubation trough. Usually, an analytical reagent is present on the front side or the test strip is coated with an analytical reagent on the front side.

In the course of a detection method of medical laboratory diagnostics making use of an aforementioned test strip and an incubation trough, more than one reagent liquid is customarily employed. After inserting the test strip into the incubation trough, first of all a first reagent liquid is introduced into the incubation trough and the test strip is exposed to this reagent liquid, and after a certain time, which may be dictated by the maker of the test strip or the test method, the reagent liquid is to be removed once more from the incubation trough. In a further step, it may then be provided to place a further reagent liquid in the incubation trough in order to then expose the test strip to this further reagent liquid, while at a still later time it may be provided to once more remove this reagent liquid as well from the incubation trough. After performing such processing steps, the test strip can then be removed from the incubation trough in order to carry out a finding or diagnosis by means of evaluation or observation of the test strip. Usually the detection of diagnostically relevant antibodies is done by way of a so-called stepwise diagnostics, in which at first a sensitive screening is performed and then a specific confirmation. In routine serology, ELISA (enzyme-linked immunosorbent assay) is often used for the screening, while immuno-blot strips are primarily used as the confirmation test, especially Western blot strips, dot blot strips, or line blot strips.

Since there is an appreciable demand for such test systems and the reagents used are often high-priced, hard to get, and only available in small amounts, a simplification and optimization of the procedures for performing such tests is essential. In particular, the analytical and diagnostic implements used must enable as much as possible a trouble-free and simple parallel performance of multiple tests at a high throughput rate. Each simplification of method, maintenance, or cleaning steps, each elimination of danger sources, no matter how slight, and each minimization of the amounts of reagents to be used results in considerable savings for the user.

In the prior art, a number of incubation troughs have been described and can be used for various analytical and diagnostic test systems or tests.

The patent application EP 3025780 A1 of the applicant describes configurations of incubation troughs where a plurality of incubation troughs can be brought together by means of mutually corresponding fastening means of the respective incubation troughs to form an assemblage of incubation troughs in the form of an incubation tray.

Moreover, it is known from patent application EP 3025779 A1 of the applicant how to provide holding elements in the form of protrusions sticking out from walls of the incubation trough for the securing or positioning of the test strip in the bottom area of the incubation trough.

SUMMARY OF THE INVENTION

The problem which the present invention proposes to solve is to make possible a combining of a test strip with reagent liquid to minimize the reagent liquid to be used so as to enable savings for the user, since reagents are at times high-priced.

The problem according to the invention is solved by an elongated incubation trough according to the various embodiments described below.

The proposed elongated incubation trough has an indentation open toward a top end of the incubation trough, extending along a longitudinal direction of the incubation trough. Moreover, the incubation trough has a bottom, which bounds the indentation toward a lower end of the incubation trough. The indentation has a first receiving area to receive an elongated test strip. In a preferred receiving of the test strip in the first receiving area, the test strip faces toward the bottom with its back side and is coated with at least one analytical reagent on its front side. According to the invention, the indentation moreover has a second receiving area, which is designed to receive an end section of a fluid line, the second receiving area being in fluidic communication with the first receiving area. According to the invention, it is provided that a width of the second receiving area at bottom height is greater than a width of the first receiving area at bottom height.

The present invention includes the following embodiments.

1. Elongated incubation trough (IR),
having an indentation (V) open toward a top end (OS) of the incubation trough (IR), extending along a longitudinal direction of the incubation trough (IR), as well as a bottom (B), which bounds the indentation (V) toward a lower end (US) of the incubation trough (IR),
wherein the indentation (V) has a first receiving area (A1) to receive an elongated test strip (T),
characterized in that the indentation (V) moreover has a second receiving area (A2) to receive an end section (EA) of a fluid line (FL), the second receiving area (A2) being in fluidic communication with the first receiving area (A1),
and moreover in that a width (BR2) of the second receiving area (A2) at bottom height (BH) is greater than a width (BR1) of the first receiving area (A1) at bottom height (BH).

2. Incubation trough according to embodiment 1,
wherein the test strip when received in the first receiving area is facing by its back side (RS) toward the bottom (B) and moreover its front side (VS) is coated with at least one analytical reagent.

3. Incubation trough (IR) according to embodiment 1,
characterized in that the bottom (B) has a continuously constant bottom height (BH) along the first receiving area (A1) and along the second receiving area (A2).

4. Incubation trough (IR) according to embodiment 1,
characterized in that the bottom (B) is formed along a two-dimensional bottom plane (BE),
and moreover in that a lateral boundary of the first receiving area (A1) is formed along the longitudinal direction by two respective, mutually facing longitudinal walls (W1, W2), wherein at least one of the longitudinal walls (W1) runs at a slant to the bottom plane (BE) such that the first receiving area (A1) narrows from the top end (OS) toward the bottom (B).

5. Incubation trough (IR) according to embodiment 4,
characterized in that both of the longitudinal walls (W1, W2) are slanted to the bottom plane (BE), so that the first receiving area (A1) has a cross section (Q) with a conical extent from the top end (OS) to the bottom plane (BE).

6. Incubation trough according to embodiment 1,
characterized in that the second receiving area (A2) is situated at an end region (EB) of the indentation (V) of the incubation trough (IR).

7. Incubation trough according to embodiment 6,
characterized in that the second receiving area (A2) is bounded on the end side at the end region (EB) by a transverse wall (QW), which extends from the bottom (B) of the second receiving area (A2) upward to the top end (OS) and extends substantially transversely to the longitudinal direction of the incubation trough (IR),
and in that the transverse wall (QW) has an obtuse angle (QWI) larger than 90° with respect to the bottom (B) of the second receiving area (A2).

8. Incubation trough according to embodiment 1,
characterized in that the second receiving area (A2) has, in a transition (UB) from the second receiving area (A2) to the first receiving area (A1), at least one curvature (R1, R2), preferably on the bottom plane (BE), which narrows from the second receiving area (A2) to the first receiving area (A1).

9. Incubation trough according to embodiment 1,
characterized in that the width (BR2) of the second receiving area (A2) at bottom height is at least 4.5 mm,
and in that the width of the first receiving area (A1) at bottom height is less than 3 mm.

10. Incubation trough according to embodiment 1,
characterized in that the first receiving area (A1) has a width (BR1) of at least 6 mm at its top end (OS, OS1).

11. Incubation trough according to embodiment 4,
characterized in that the at least one longitudinal wall (W1) makes an angle (WW1) of at least 7° with a normal (FN) to the surface of the bottom plane (BE).

12. Incubation trough according to embodiment 7,
characterized in that the transverse wall (QW) makes an angle (QWI) in the range of 110° to 150° with the bottom (B) of the second receiving area (A2).

13. Incubation tray (IW) with a plurality of incubation troughs (IR1, IR2) according to one of the preceding embodiment, preferably arranged parallel to each other.

14. Incubation tray according to embodiment 13,
wherein two of the parallel arranged incubation troughs (IR1, IR2) each have a respective centre axis (MA1, MA2) in the longitudinal direction,
characterized in that the respective centre axes (MA1, MA2) have a spacing (AB) from each other in the range of 8.5 mm to 9.5 mm.

15. System
with an incubation trough according to one of embodiments 1 to 12
and moreover with at least one test strip, which is coated on at least one side with at least one analytical reagent.

16. Use of a system according to embodiment 15 for the detection of biological material.

BRIEF DESCRIPTION OF THE DRAWINGS

FIG. 1a shows an incubation trough according to a preferred embodiment in a front view.

FIG. 1b shows a first sectional view of the embodiment of the incubation trough.

FIG. 1c shows a second sectional view of the embodiment of the incubation trough.

DETAILED DESCRIPTION OF THE INVENTION

Figure 2:
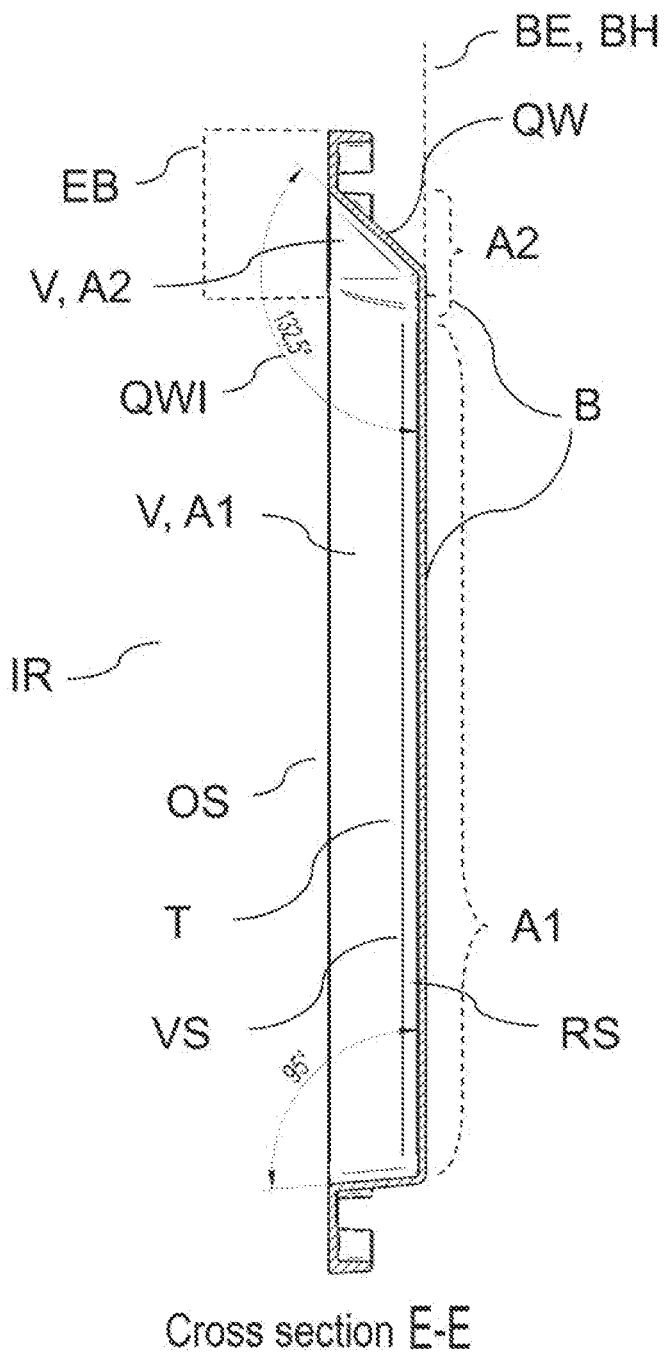
FIG. 2 shows a side view of the embodiment of the incubation trough.

In order to comprehend one or more possible benefits of the invention, the mode of functioning of the proposed incubation trough shall first be explained more closely below.

As mentioned above, it is customarily necessary, after placing a reagent liquid in the incubation trough in order to expose the test strip to this reagent liquid, also to remove this reagent liquid from the incubation trough once more after a certain time, for example in order to halt a reaction between the reagent liquid and an analytical reagent present on the front side of the test strip. For this, it may be provided, by means of a fluid line of an automatic instrument or by using a pipette, to introduce an end section of such a fluid line into the second receiving area and then aspirate the reagent liquid or the major portion of the reagent liquid out from the indentation of the incubation trough. Such end sections of fluid lines for receiving a reagent liquid usually have a certain minimum width in order to ensure a minimum flow amount per unit of time. If the first and the second receiving area were to have the same common width, oriented solely to the minimum width of the fluid line, then the width of the end section of the fluid line and the width of the second receiving area would also dictate the width for the first receiving area and thus have a determining influence on the volume of the first receiving area. Since generally a certain minimum fill height of the first receiving area is necessary for an adequate contacting of the test strip with reagent liquid, the minimum width of the fluid line and the width of the second receiving area being the same width as the first receiving area would then also have a significant influence on the amount of reagent liquid to be used. In other words: the width of the second receiving area would also determine the volume of the first receiving area and thus also the volume of reagent liquid to be used.

Because according to the invention the first receiving area is designed to receive the test strip and has a lesser width than the width of the second receiving area, which is designed for the separate receiving of the end section of the fluid line, it is possible:

on the one hand, to ensure that the width of the second receiving area has a minimum width for an end section of a fluid line and thus a minimum flow amount per unit of time can be aspirated, and moreover it can be assured that a volume of the first receiving area in which the test strip is located is minimized or reduced.

Thus, in this way the necessary amount of reagent liquid for the covering of the test strip can be minimized or reduced overall, without placing new demands on end sections of fluid lines or attached pumps for the fluidic delivery of the reagent liquid.

The incubation troughs known in the prior art are designed such that they have a substantially constant width, especially at a bottom height of the incubation trough. Therefore, it may happen in the prior art that the constant width provided there determines the overall volume in which reagent liquid must be introduced in order to adequately cover the test strip. Generally, a certain fill height of the incubation trough is needed for this. Because the incubation trough according to the invention is more narrow in the first receiving area than in the second receiving area, the necessary fill height of the incubation trough is achieved already at a lesser volume amount of reagent liquid than in the prior art, while still also assuring that a typical end section of a fluid line with a typical dimensioning can be introduced into the second receiving area.

Advantageous embodiments of the invention are the subject matter of the dependent embodiments and shall be explained more closely in the following description, making reference at times to the figures.

Preferably the second receiving area may also be provided to receive an end section of a fluid line for a procession step, in order to introduce reagent liquid into the indentation.

Preferably in the context of this application the width of a receiving area means the respective maximum width of the respective receiving area.

Preferably the test strip when received in the first receiving area is facing by its back side toward the bottom and moreover its front side is coated with at least one analytical reagent.

Preferably the incubation trough is outfitted with the test strip.

Preferably the incubation trough is characterized in that the bottom has a continuously constant bottom height along the first receiving area and along the second receiving area.

Preferably the bottom is formed along a two-dimensional bottom plane, while moreover a lateral boundary of the first receiving area is formed along the longitudinal direction by two respective, mutually facing longitudinal walls, wherein at least one of the longitudinal walls runs at a slant to the bottom plane such that the first receiving area narrows from the top end toward the bottom.

Preferably both of the longitudinal walls are slanted to the bottom plane, so that the first receiving area has a cross section perpendicular to the longitudinal direction with a conical extent from the top end to the bottom plane.

Preferably the second receiving area is situated at an end region of the indentation of the incubation trough.

Preferably the second receiving area is bounded on the end side at the end region by a transverse wall, which extends from the bottom of the second receiving area upward to the top end and extends substantially transversely to the longitudinal direction of the incubation trough, the transverse wall making an obtuse angle larger than 90° with respect to the bottom of the second receiving area.

Preferably the second receiving area has, in a transition from the second receiving area to the first receiving area, at least one curvature, preferably on the bottom plane, which narrows from the second receiving area to the first receiving area.

Preferably the width of the second receiving area at bottom height is at least 4.5 mm and the width of the first receiving area at bottom height is less than 3 mm.

Preferably the first receiving area has a width of at least 6 mm at its top end.

Moreover, there is proposed an incubation tray with a plurality of incubation troughs, preferably arranged parallel to each other, being configured according to the invention or according to one of the advantageous embodiments.

Preferably two of the parallel arranged incubation troughs each have a respective centre axis or axis of symmetry in the longitudinal direction, while the respective centre axes or axes of symmetry have a spacing from each other in the range of 8.5 mm to 9.5 mm.

In one preferred embodiment, the term "test strip" as used herein is understood to be a preferably elongated substrate, which is sufficiently chemically inert to conventional solvents, especially water-based solvents, and which is coated with a reagent, which is suitable for a desired chemical reaction, especially an analytical method, especially preferably a laboratory diagnostic method. The material of the test strip can be a membrane, which is capable of receiving or binding biological material. In various embodiments of the invention, the test strip comprises or consists of nitrocellulose or polyvinylidene fluoride (PVDF). A biological material is preferably bound to a test strip. The biological material is preferably chosen from the group consisting of peptides/proteins, lipids, nucleic acids, saccharides, combinations and fusion molecules of these. In further preferred embodiments, the biological material is a peptide/protein possessing a length of 2-500 amino acids (AA), 5-450 AA, 10-400 AA, 20-350 AA, 30-300 AA, 50-250 AA, 80-200 AA, 100-150 AA or 115-135 AA. Moreover, the biological material is preferably deposited in discrete bands on the test strip material and the biological material moreover preferably has a fraction of at least 50, at least 60, at least 70, at least 80, at least 85, at least 90, at least 95, at least 97, at least 99 or 100 wt. % in regard to the total weight and/or mol. % in regard to the total composition of the bands. Preferably, the test strip material and the biological material can be a nitrocellulose strip with an antigen.

In one preferred embodiment, the term "elongated" as used herein is understood to mean that the length ratio of the longer to the shorter side is at least 5:1, 7.5:1, 10:1, 15:1 or more, in order of increasing preference.

In another preferred embodiment, the term "coated" as used herein is understood to mean that the reagent is connected to the test strip such that a liquid standing in contact with the front side of the strip also makes contact with the reagent. For example, the reagent may be blotted or applied or dispensed on the surface of the front side, or the test strip may have a substantially uniform concentration of the reagent at all places. Suitable test strips are described in the prior art and available in commerce, such as line blots of the company EUROIMMUN Medizinische Labordiagnostika AG, Lübeck.

In one preferred embodiment, the term "analytical reagent" as used herein is understood to mean a chemical compound which reacts chemically or physically with an analyte contained in a specimen or other aqueous solution to be investigated. This reaction can be detected. For example, the analytical reagent is an antigen, especially an epitope-containing polypeptide, to which an antibody to be detected, preferably an auto-antibody, from a specimen to be investigated binds, whereupon the resulting antigen-antibody complex can be detected by means of another enzyme-conjugated antibody. Alternatively, the analytical reagent may be a pH-dependent stain, taking on a particular indicative colour when exposed to a solution with a particular pH value.

In one preferred embodiment, the term "incubation trough" as used herein is understood to mean a preferably liquid-tight container with a bottom, two longitudinal walls and two transverse walls. The incubation trough is elongated in shape so as to receive a test strip. In the case of an incubation trough of rectangular periphery, the length ratio of transverse wall to longitudinal wall is at least 1:5, 1:10 or larger. Preferably, the incubation tray consists of a material resistant to aqueous solutions, such as polystyrene, polyethylene or polypropylene. In one preferred embodiment, the incubation tray is outfitted with a test strip and, optionally, contained in a package.

A "test strip" can preferably be a blot strip, having reagents which may be suitable for a detection of gangliosides, as is known from patent application EP2952898 A1. Moreover, a "test strip" may preferably be a blot strip having reagents which may be suitable for a detection of macadamia, as is known from patent application EP3196209 A1. Moreover, a "test strip" may preferably be a blot strip having reagents which may be suitable for a detection of Echinococcus, as is known from patent application EP3156798. Moreover, a "test strip" may preferably be a blot strip having reagents which may be suitable for a detection of Ara h 7 isotype 7.0201, as is known from patent application EP3244212 A1.

In another preferred embodiment, the incubation trough contains, besides the test strip, a liquid. This may be a sample to be investigated, a washing solution, or a solution with chemical reagents, preservatives, or analytes.

The incubation trough may be used purely manually by manual insertion and removal of the required reagents for chemical reactions, especially analytical or diagnostic tests. Preferably, however, the incubation trough or the assemblage will be placed in a device which performs numerous steps, ideally all of the steps, fully automatically, as much as possible without requiring technical staff being present. Such a device is outfitted for stockpiling as well as introducing and aspirating suitable buffers and reagents, ideally also for making suitable photographs of the fully processed test strip.

Figure 3:
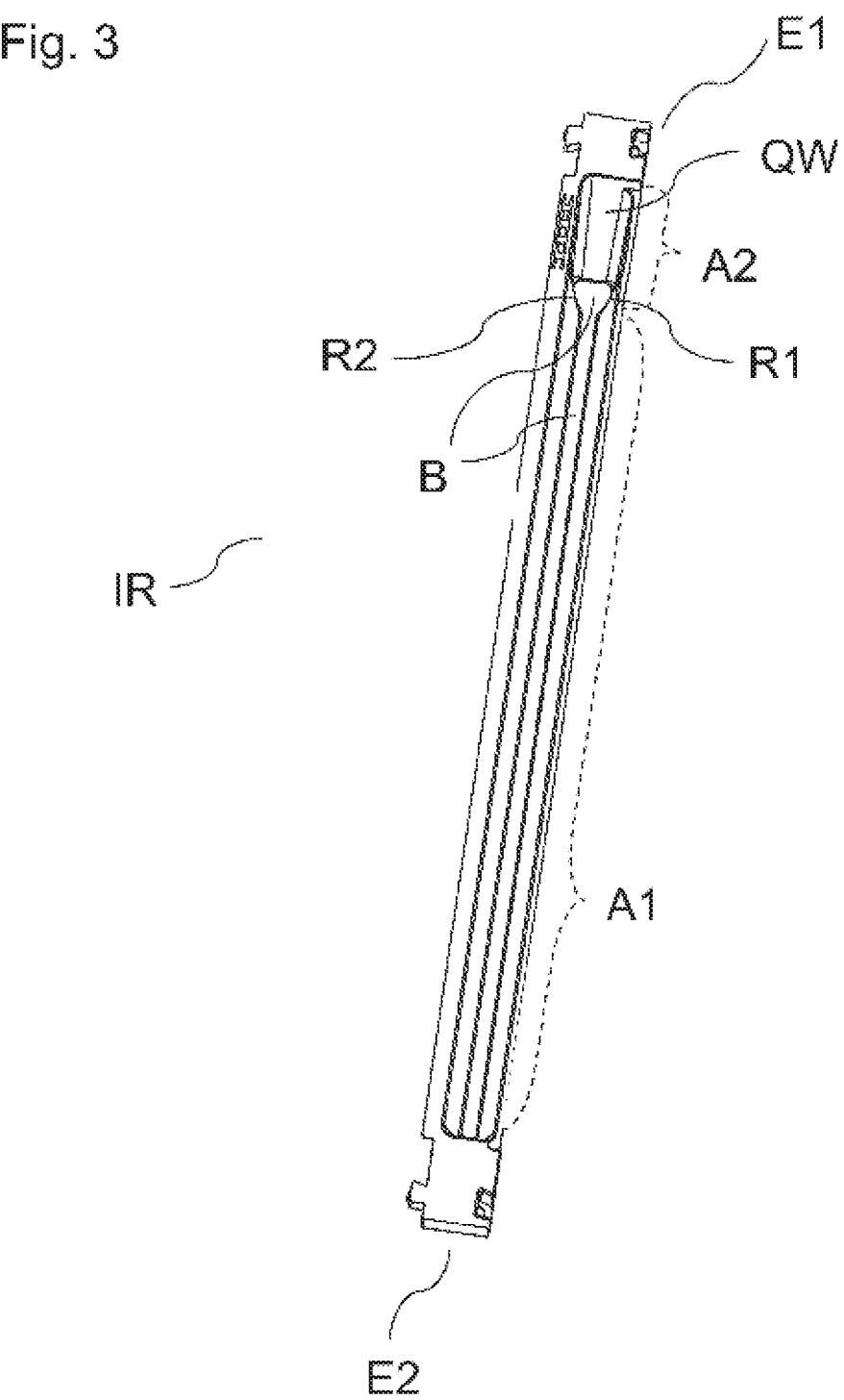
FIG. 3 shows a slanted view of the embodiment of the incubation trough.
Figure 4:
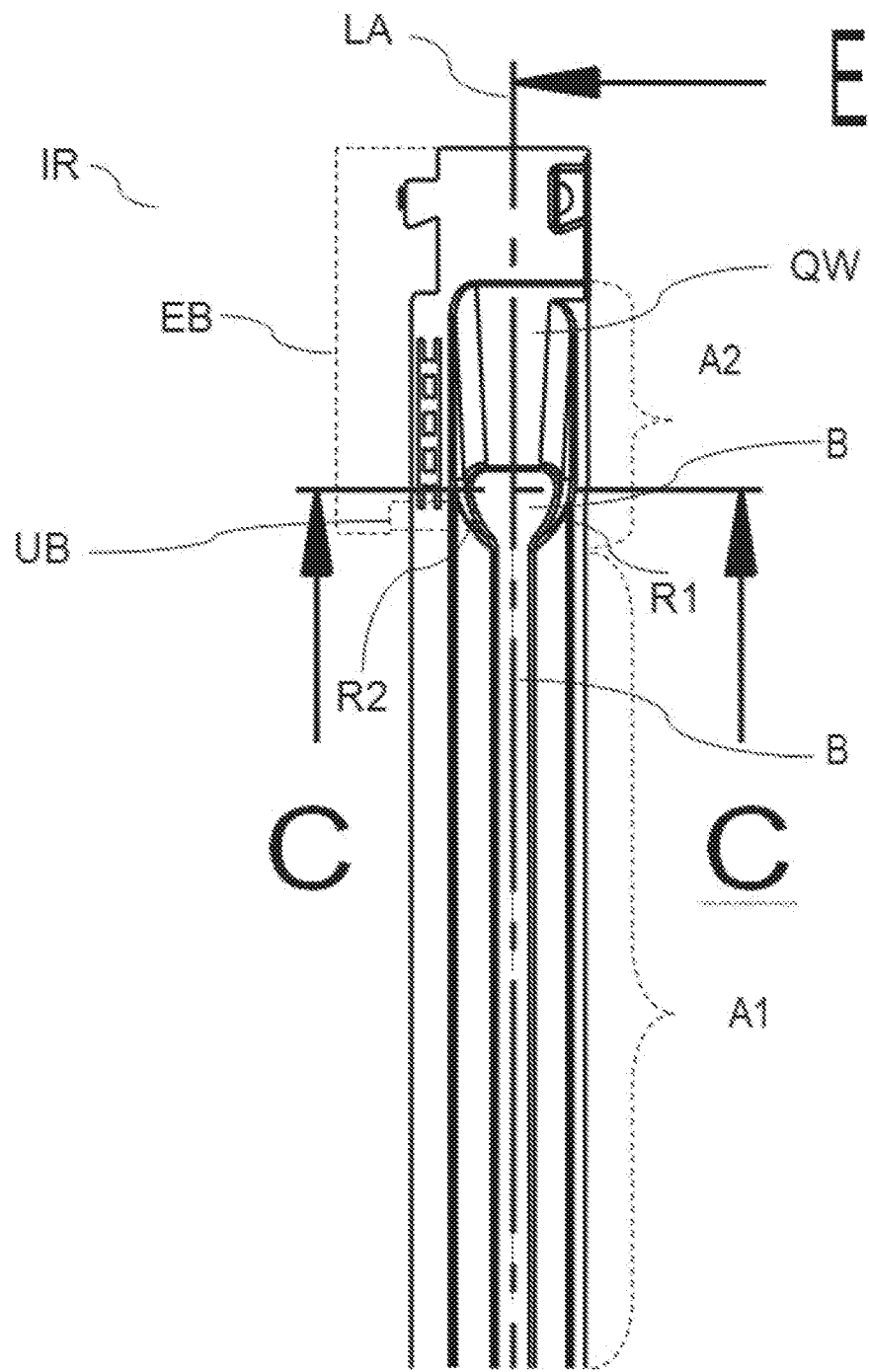
FIG. 4 shows a detail view of the embodiment of the incubation trough.
Figure 5:
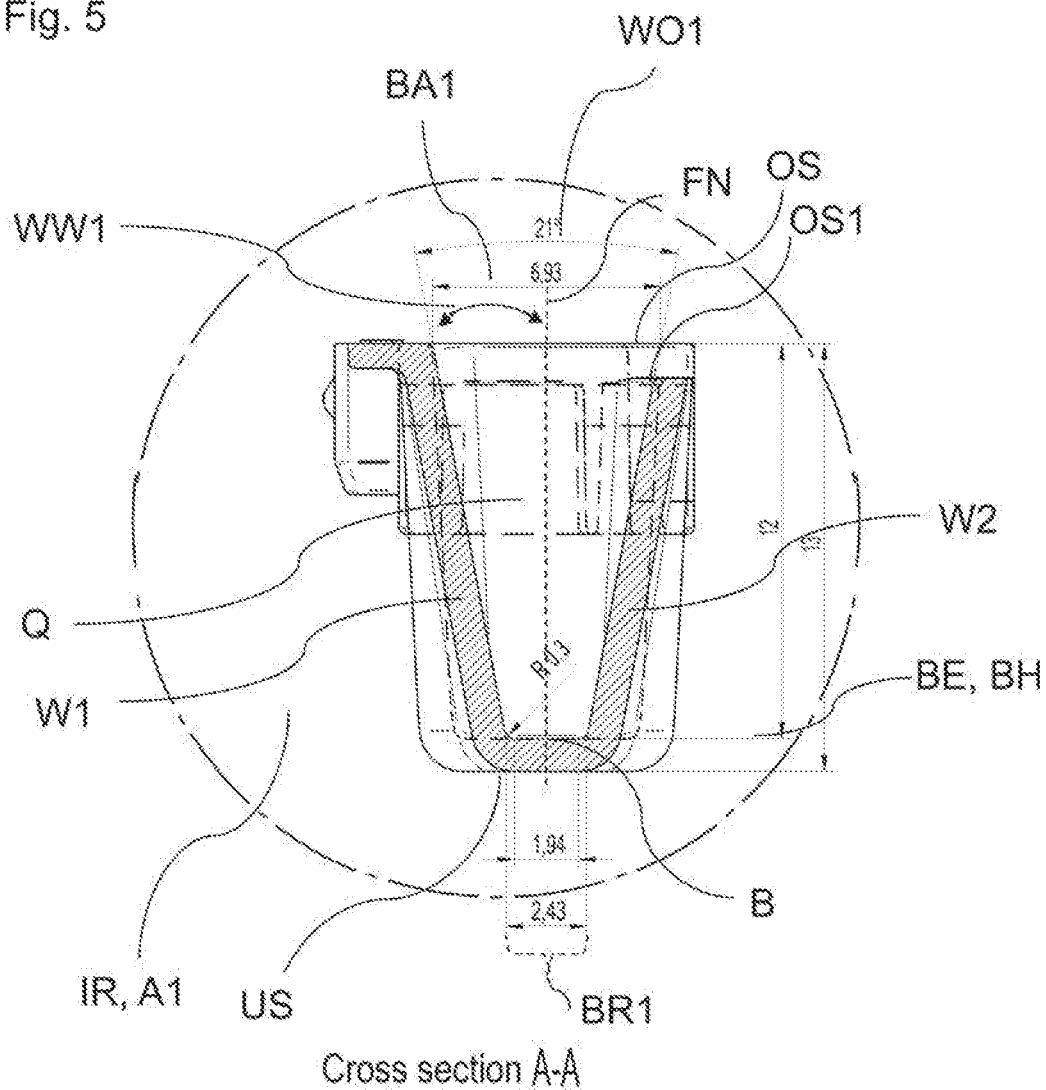
FIG. 5 shows the first sectional view of the embodiment of the incubation trough in detail.
Figure 6:
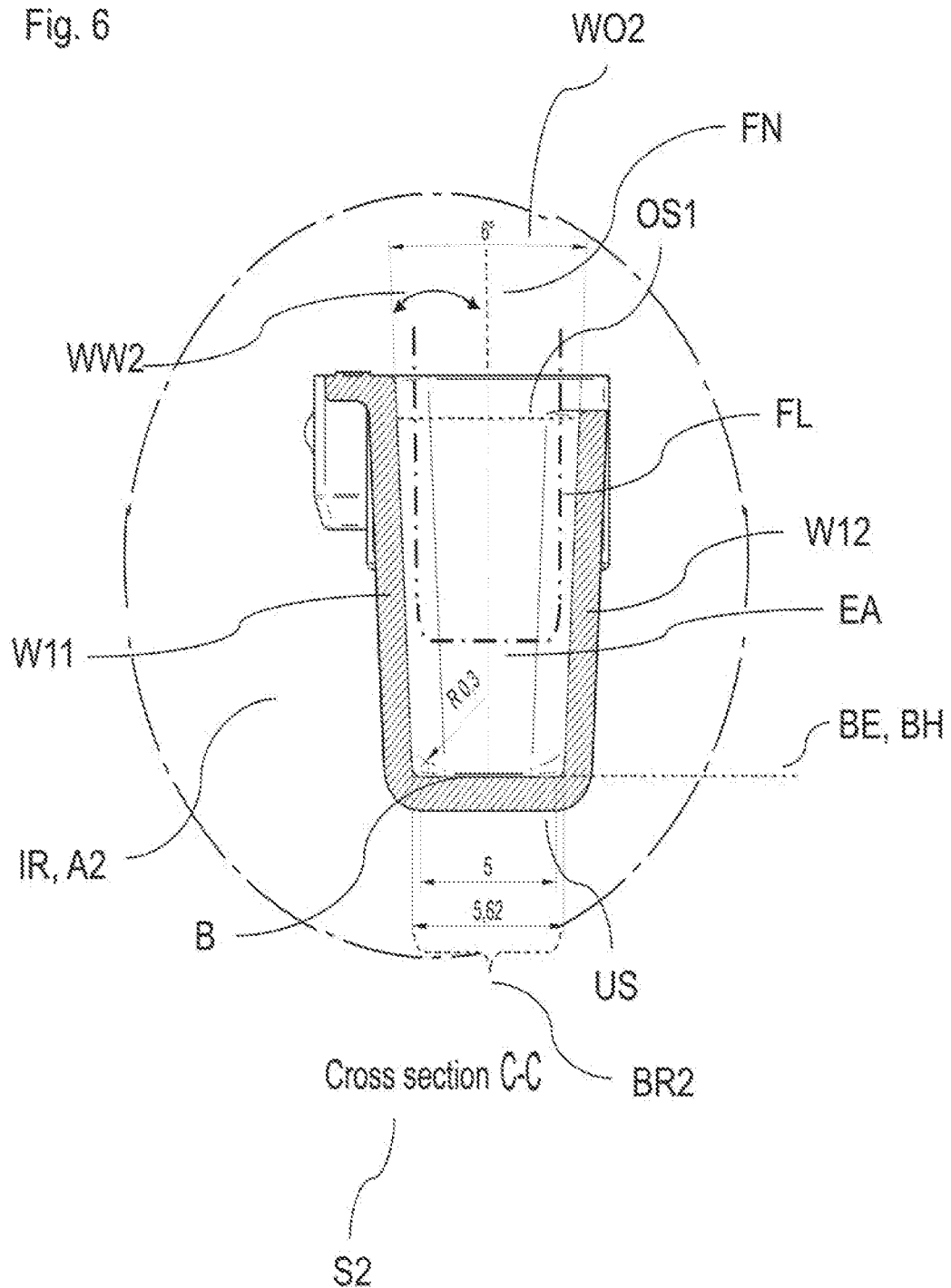
FIG. 6 shows the second sectional view of the embodiment of the incubation trough in detail.
Figure 7:
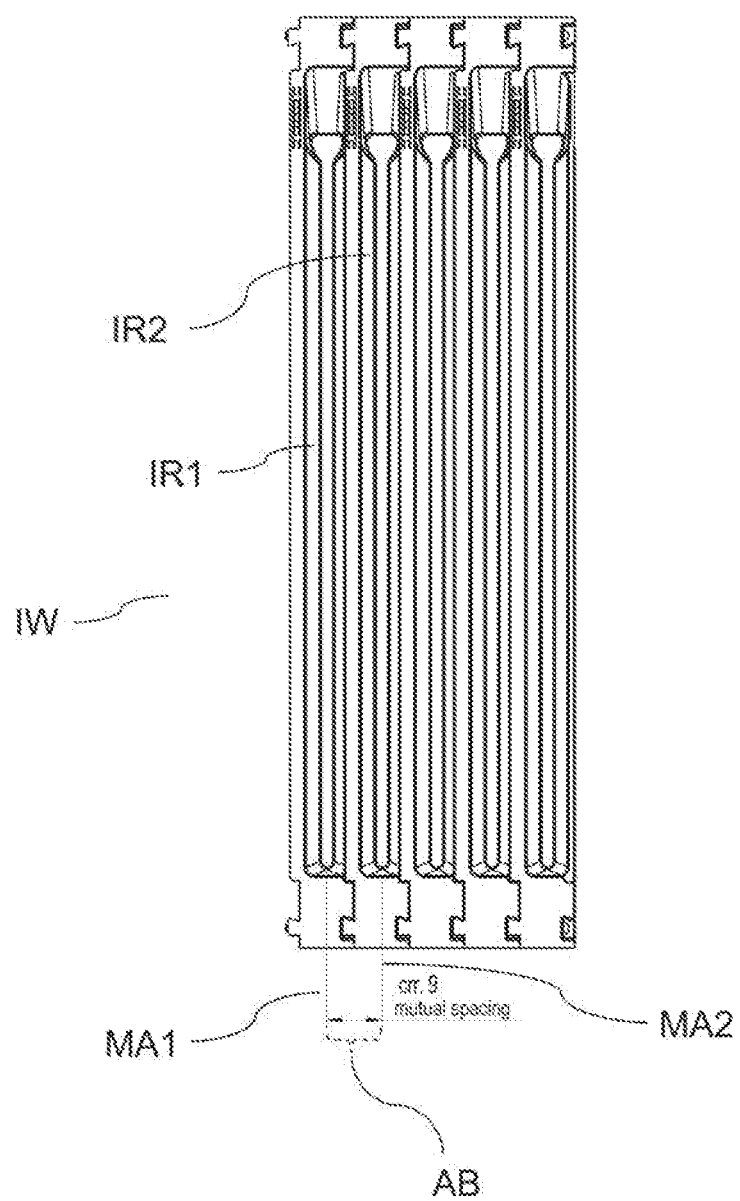
FIG. 7 shows a preferred embodiment of an incubation tray in a front view.
Figure 8:
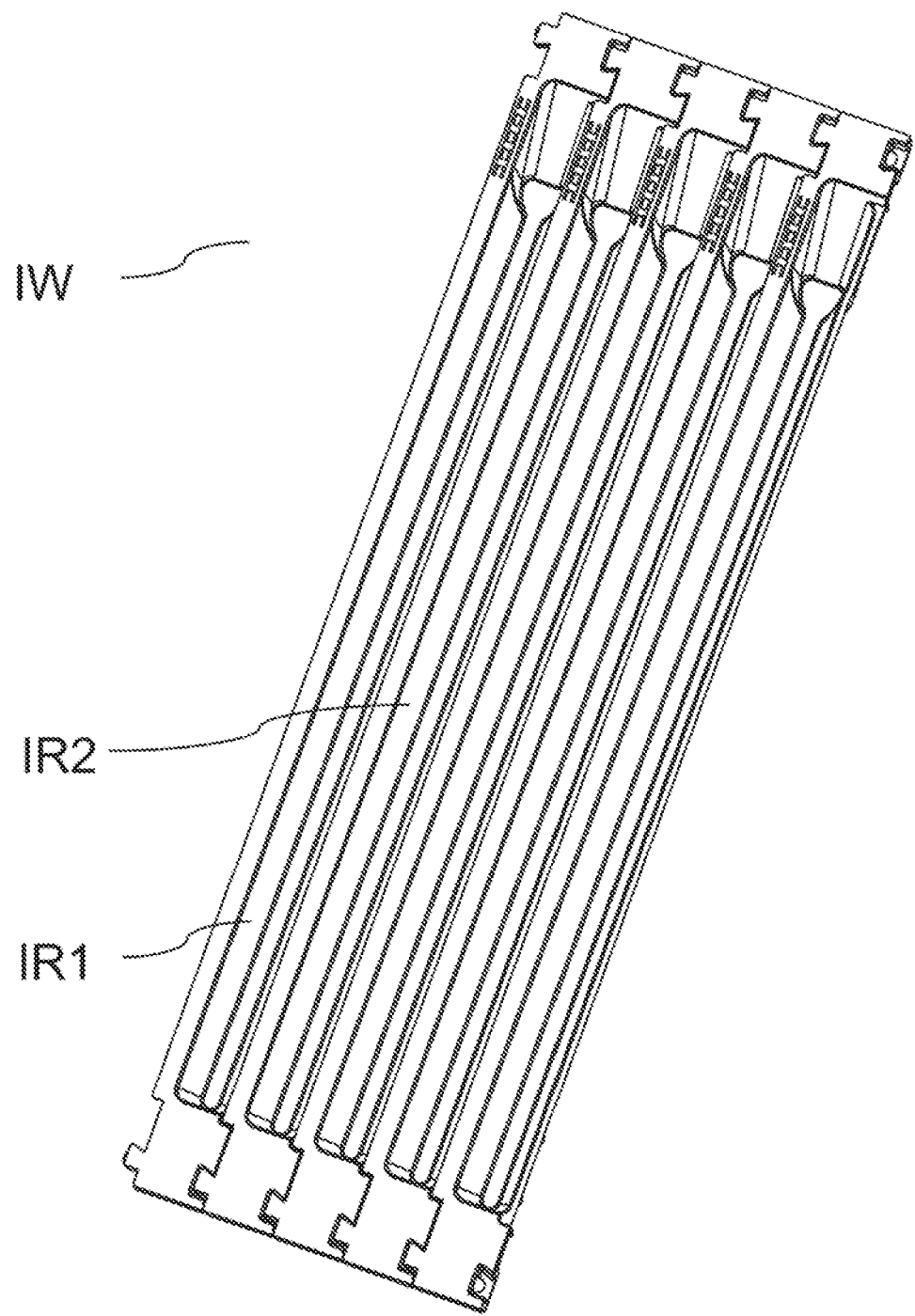
FIG. 8 shows a slanted view of the embodiment of the incubation tray.

In the following, the invention shall be explained more closely with the aid of special embodiments, without limiting the general notion of the invention, making use of the figures. There are shown:

FIG. 1a, an incubation trough according to a preferred embodiment in a front view, FIG. 1b, a first sectional view of the embodiment of the incubation trough, FIG. 1c, a second sectional view of the embodiment of the incubation trough, FIG. 2, a side view of the embodiment of the incubation trough, FIG. 3, a slanted view of the embodiment of the incubation trough, FIG. 4, a detail view of the embodiment of the incubation trough, FIG. 5, the first sectional view of the embodiment of the incubation trough in detail, FIG. 6, the second sectional view of the embodiment of the incubation trough in detail, FIG. 7, a preferred embodiment of an incubation tray in a front view, FIG. 8, a slanted view of the embodiment of the incubation tray.

FIG. 1a shows an incubation trough IR, which extends in the longitudinal direction along a longitudinal axis LA.

The incubation trough IR has an indentation V, the indentation V in turn having a first receiving area A1 and a second receiving area A2. The first receiving area A1 is designed to receive an elongated test strip. The second receiving area A2 is designed to receive an end piece of a fluid line. The second receiving area A2 is situated preferably in an end region EB of the incubation trough IR. The incubation trough IR may be turned or swivelled about its transverse axis QA, which is perpendicular to the longitudinal axis LA, in order to bring about an exchange of reagent liquid between the first receiving area A1 and the second receiving area A2. Moreover, by turning back and forth about the transverse axis QA, a distribution of reagent liquid in the first receiving area A1 can be produced so as to fully bring a test strip located in the first receiving area A1 into contact with reagent liquid.

FIG. 1b shows a first sectional view S1 of the incubation trough along a sectioning axis A-A, as shown in FIG. 1a. FIG. 1b shows the indentation V of the incubation trough IR in the region of the first receiving area A1. The indentation V of the incubation trough IR is bounded by a bottom B toward the lower end US of the incubation trough IR.

FIG. 1c shows a second sectional view S2 along the axis C-C, as shown in FIG. 1a. FIG. 1c shows the indentation V of the incubation trough IR in the region of the second receiving area A2. The indentation V of the incubation trough IR is also bounded here by a bottom B toward the lower end US of the incubation trough IR.

These sectional views S1, S2 are shown in greater detail in FIGS. 5 and 6 and shall be explained more closely below.

FIG. 2 shows the proposed incubation trough IR in a side view at a section along the longitudinal axis LA and along points E-E from FIG. 1a. Here as well, the first receiving area A1 can be clearly recognized, in which a test strip T is preferably placed, being inserted with its back side RS toward the lower end US or bottom B of the incubation trough. Usually the test strip T is coated on its front side VS with an analytical reagent. The test strip T is not necessarily part of the proposed incubation trough IR, but preferably it may be such. The test strip T which is represented in FIG. 2 and which is preferably present is not shown explicitly in FIGS. 1a, b, c as well as 3 to 8.

As can be clearly seen here, the indentation V is formed substantially through the first receiving area A1 into the second receiving area A2. The incubation trough IR is bounded at the end side in the second receiving area A2 by a transverse wall QW.

Moreover, FIG. 2 shows a bottom plane BE or bottom height BH, along which the bottom B extends.

FIG. 3 shows the proposed incubation trough IR yet again in a slanted view.

FIG. 5 shows the sectional view S1 and thus a cross section of the first receiving area A1 or the indentation V from FIG. 1a along the axis A-A. The width BR1 of the bottom B is the width resulting for the indentation or the first receiving area at the bottom height BH or bottom plane BE.

FIG. 6 shows the sectional view S2 and thus a cross section of the second receiving area A2 or the indentation V from FIG. 1a along the axis C-C. The width BR2 of the bottom B is the width resulting for the indentation or the first receiving area at the bottom height BH or bottom plane BE.

If one compares the width BR1 of the first receiving area A1 from FIG. 5 with the width BR2 of the second receiving area A2 from FIG. 6, it will be apparent that the width BR2 of the second receiving area A2 at bottom height BH or the bottom plane BE is larger than the width BR1 of the first receiving area A1. This different dimensioning of the width BR1 of the first receiving area A1 at bottom height and the width BR2 of the second receiving area A2 at bottom height produces the benefit explained in detail above, that the overall volume of the indentation V, also see FIGS. 1a and 2, is reduced as compared to an embodiment of an incubation trough not represented here, in which a common and identical or constant width for both receiving areas would be dictated by a width of a fluid line or its end section.

FIG. 6 shows in dotted representation a fluid line FL, which is introduced by its end section EA into the second receiving area A2, for example in order to aspirate reagent liquid or else to introduce reagent liquid into the indentation.

FIG. 3 shows the bottom B, which according to the embodiment shown here has a continuously constant bottom height BH, as drawn in FIGS. 5 and 6, both in the region of the first receiving area A1 and that of the second receiving area A2. In this way, a fluidic coupling between these two receiving areas A1, A2 is maximized, so that reagent liquid can be exchanged especially easily between these two receiving areas A1, A2. For example, in the course of a processing it is customary to turn the incubation trough about the transverse axis QA, shown in FIG. 1a, so that the reagent liquid moves back and forth between the ends E1, E2 of the incubation trough IR. In this way, reagent liquid will be placed equally onto the surface of the test strip.

Thanks to the continuously constant bottom height BH, which is also drawn in FIGS. 5 and 6, the reagent liquid can pass especially easily from the second receiving area A2 into the first receiving area A1 and back again. If at a later time, in a later processing step, the reagent liquid is then aspirated by means of an end section of a fluid line, which can be introduced into the second receiving area A2, the constant bottom height also ensures that a maximum of reagent liquid can be removed from the indentation V or the receiving areas A1, A2. Hence, it is ensured that, after such an aspiration step, only a minimum of reagent liquid remains in the incubation trough, before a new, further reagent liquid for a further processing step is then preferably introduced into the incubation trough or its second receiving area A2.

In other words, it may be said that the bottom B for the first and the second receiving area A1, A2 is formed along a two-dimensional bottom plane BE, as is drawn in FIGS. 5 and 6.

In still other words, it may be said that the bottom B extends along both receiving areas A1, A2 with a constant bottom height on a common two-dimensional bottom plane of the two receiving areas A1, A2 as a continuous surface across these two receiving areas A1, A2.

FIG. 5 shows, besides the bottom B in the first receiving area, also a lateral boundary of the first receiving area along the longitudinal direction formed by two respective, mutually facing longitudinal walls W1, W2. At least one of the longitudinal walls W1 extends at a slant to the bottom plane BE or the bottom B such that the first receiving area A1 narrows from the top end OS of the incubation trough IR or the first receiving area A1 to the lower end US of the incubation trough IR. Hence, a width BA1 of the first receiving area A1 at the top end OS is larger than the width BR1 of the first receiving area A1 at the bottom B or at the bottom height BH.

Because the first receiving area A1 narrows from the top end OS toward the lower end US or toward the bottom B, it is easier to insert a test strip, which is only slightly narrower than the bottom of the first receiving area, from the top end OS into this first receiving area A1 than if both longitudinal walls W1, W2 were perpendicular to the bottom plane BE and would form a constant width of the first receiving area A1 that is only slightly broader than the test strip at any given height. In such a case of a constant width of the first receiving area A1, the user would then have to position or orient the test strip very precisely with respect to the height of the top end OS in relation to a longitudinal direction, a transverse direction, and/or a rotation when introducing it into the first receiving area A1, so that the test strip can then be introduced correctly into the first receiving area A1. Because at least one of the longitudinal walls W1, W2 runs slanted to the bottom plane BE and the first receiving area A1 narrows from the top end OS toward the bottom B, so that a width of the first receiving area A1 at the top end OS is greater than the width of the first receiving area BA1 at bottom height BH or at the bottom B, the test strip can be introduced more easily by the user, since in this way a tolerance compensation achieves a positioning of the test strip with respect to the first receiving area A1.

Preferably both longitudinal walls W1, W2 are slanted with respect to the bottom plane BE so that a conical extent of the cross section Q of the first receiving area A1 from the top end OS toward the bottom plane BE or toward the bottom B is produced. Preferably the cross section Q is symmetrical to a centre axis or surface normal FN, which stands orthogonally to the bottom plane BE. This accomplishes the aforementioned tolerance compensation when positioning the test strip relative to the first receiving area A1 in both directions or to the left and right in the same way.

FIG. 1a moreover shows that the second receiving area A2 is located at one end region EB of the indentation V of the incubation trough. This end region EB and further details about this are shown more precisely in FIG. 4.

FIG. 4 shows that the second receiving area A2 is bounded at the end side at the end region EB by a transverse wall QW, which runs from the bottom B of the second receiving area A2 upward toward the top end of the second receiving area or the incubation trough IR. The transverse wall QW moreover runs substantially transversely to the longitudinal direction of the incubation trough IR. The transverse wall QW is moreover drawn in FIG. 3 as well as in FIG. 2. According to FIG. 2, the transverse wall QW makes an obtuse angle QWI greater than 90° with the bottom B of the second receiving area A2.

If reagent liquid is present in the incubation trough and at the end of a processing step the incubation trough is turned or tilted by its transverse axis toward the end region EB of the incubation trough IR, a larger amount of reagent liquid can be received in the second receiving area A2 thanks to the proposed configuration of the transverse wall QW or its extent than if the transverse wall QW were perpendicular to the bottom B or the bottom plane BE.

FIG. 4 further shows a transitional region or a transition UB of the second receiving area A2, bordering on the first receiving area A1. The second receiving area A2 has respective narrowing curvatures R1, R2 in the transition UB from the second receiving area A2 to the first receiving area A1, preferably at the height or level of the bottom B.

Such a configuration of the transition UB makes it possible to maximize the passage of reagent liquid from the second receiving area A2 to the first receiving area A1 despite different widths of the receiving areas A1, A2 at the bottom plane or bottom height. If there were for example a polygonal configuration of the transitional region UB between the receiving areas A1, A2 due to right-angled corners in the transitional region UB, reagent liquid would flow less easily from the second receiving area A2 to the first receiving area A1. Moreover, the avoidance of corner regions with angles of 90° or less than 90° at the height of the bottom B or on the bottom plane BE as proposed here is advantageous, since in such corner regions a reagent liquid might form greater forces of adhesion by surface tension than in round shaped margin regions, so that reagent liquid might remain in the second receiving area A2 and be even unable to pass over into the first receiving area A1. This would produce an inhomogeneous distribution of reagent liquid in the indentation and thus also in the receiving areas A1, A2 during a processing step, so that a homogeneous or uniform coverage of the test strip with reagent liquid might not be achieved.

The width BR2, drawn in FIG. 6, of the second receiving area A2 is advantageously at least 4.5 mm, preferably at least 5 mm, more preferably at least 5.5 mm. This width BR2 of the second receiving area A2 may also be called the maximum width of the second receiving area A2. The width BR1, drawn in FIG. 5, of the first receiving area A1 at bottom height amounts to preferably less than 3 mm, preferably less than 2.75 mm, even more preferably less than 2.6 mm, preferably less than 2.5 mm.

According to the embodiment of the first receiving area proposed in FIG. 5, the longitudinal walls W1, W2 have different height. Preferably these walls W1, W2 may have the same height. In the event that the wall height of the walls W1, W2 is the same, a first top end OS of the first receiving area A1 will be produced. Given a lesser height of the longitudinal wall W2 compared to the longitudinal wall W1, a further top end OS1 of the first receiving area can be defined, as drawn in FIG. 5.

For the first mentioned case of the first top end OS, a width BA1 of the first receiving area A1 is shown in FIG. 5. For the case of the longitudinal walls W1, W2 having different lengths, a corresponding width of the first receiving area can be determined for the top end OS1 drawn there. For both of these cases, it can be proposed that the first receiving area A1 has at its top end OS, OS1 a width BA1 of at least 6 mm, preferably at least 6.5 mm.

Thanks to the dimensions proposed here for the widths BR2 and BR1 of the receiving areas A2, A1 as well as the width BA1 of the first receiving area A1 at its top end OS, OS1, the volume of the indentation V or the first receiving area A1 is minimized, even while observing a minimal width dimension at the top end OS, OS1 of the incubation trough IR. Hence, the incubation trough IR proposed here can be used in a standardized automatic instrument, which may require such a minimum width.

FIG. 5 shows an aperture angle WO1, which is dictated here by an angle setting for the two longitudinal walls W1, W2. This aperture angle WO1 is the aperture angle of the indentation V in the first receiving area A1. This aperture angle is preferably 21°. Preferably the longitudinal wall W1 makes an angle WW1 of at least 7°, preferably at least 8°, more preferably at least 10° with a normal FN to the surface of the bottom plane BE or the bottom B. Preferably the same holds for the other longitudinal wall W2.

Thanks to a slanted configuration of at least one or both of the longitudinal walls W1, W2, in production methods such as the injection moulding method or deep drawing method for the making of the incubation trough from plastics one avoids problems in terms of manufacturing technology in the detaching of a manufacturing mould from the plastic. In particular, right angles between the bottom B and the walls W1, W2 might make it difficult to detach the mould from the material or the plastic.

Preferably it is proposed that the angle WW1 of the longitudinal wall W1 with respect to the normal FN to the surface of the bottom plane BE or the bottom B does not exceed the value of 20°, preferably 15°. The same may be provided for the other longitudinal wall W2. In this way, a camera evaluation or automated image evaluation of the test strip can be done by means of a viewing of the incubation trough from above, as represented in FIG. 1a, without too many interfering image artefacts. Such an image evaluation is usually done with the assistance of illuminating light which shines into the incubation trough from above, so that a back reflection of the illuminating light from the insides of the longitudinal walls W1, W2 and back to the camera is minimized in that the angle WW1 does not exceed a certain value. If a particular angle value is exceeded by the angle WW1, automated image evaluation might be impeded by such back reflection effects on the walls W1, W2. If the longitudinal walls W1, W2 were to exceed the angle values proposed here, such a back reflection effect might be present to an excessive degree, making an automated image evaluation difficult.

The angle QWI shown in FIG. 2, made by the transverse wall QW with the bottom B of the second receiving area A2, is preferably an angle in the range of 110° to 150°, preferably 120° to 140°, even more preferably 125° to 135°.

The incubation trough proposed here is preferably made by means of a plastic injection moulding process. Thanks to the dimensioning chosen here for the proposed width values and/or angle values, it becomes possible to detach the proposed incubation trough from an injection mould without significant mechanical resistance during a production by means of an injection moulding method.

Moreover, a system is proposed with an incubation trough as proposed here and moreover with a test strip as described here. Moreover, there is proposed a use of a system as proposed here for the detection of biological material, preferably by means of inserting a test strip as described here into an incubation trough as proposed here, introducing at least one reagent liquid into the incubation trough for the incubating of the test strip, removal or aspiration of the reagent liquid from the incubation trough, washing of the test strip with at least one liquid washing buffer and detecting of a formation of at least one band on the test strip for the detection of a biological material.

FIG. 7 shows a proposed incubation tray IW with a plurality of incubation troughs IR1, IR2, which are arranged preferably parallel to each other. Preferably the respective incubation troughs IR1, IR2 have fastening elements corresponding to each other, in order to obtain the incubation tray IW by joining the incubation troughs IR1, IR2 together.

FIG. 8 shows the proposed incubation tray with the incubation troughs IR1, IR2 arranged parallel to each other in a slanted view.

According to FIG. 7, the incubation troughs IR1, IR2 arranged parallel to each other each have a respective centre axis MA1, MA2 in the longitudinal direction. In the incubation tray IW proposed here, the centre axes MA1, MA2 of the incubation troughs IR1, IR2 have a spacing AB from each other, which lies preferably in the range of 8.5 mm to 9.5 mm, preferably 8.75 mm to 9.25 mm, even more preferably 8.9 mm to 9.1 mm. By observing this spacing AB of the incubation troughs IR1, IR2 or their centre axes MA1, MA2, it becomes possible to use the incubation tray IW in a standard automatic instrument, without having to adapt to the instrument or without having to provide special adapters to use the tray IW in such an instrument.

The invention claimed is:

1. An elongated incubation trough, comprising:
an indentation open toward a top end of the incubation trough, extending along a longitudinal direction of the incubation trough, as well as a bottom, which bounds the indentation toward a lower end of the incubation trough,
wherein the indentation has a first receiving area to receive an elongated test strip,
wherein the indentation has a second receiving area to receive an end section of a fluid line, the second receiving area being in fluidic communication with the first receiving area, wherein the second receiving area is situated at an end region of the indentation of the incubation trough, wherein the second receiving area is bounded on an end side at the end region by a transverse wall, which extends from the bottom of the second receiving area upward to the top end and extends substantially transversely to the longitudinal direction of the incubation trough, wherein the transverse wall has an obtuse angle larger than 90° with respect to the bottom of the second receiving area,
wherein a width of the second receiving area at bottom height is greater than a width of the first receiving area at bottom height, and
wherein the bottom is formed along a two-dimensional bottom plane,
and in that a lateral boundary of the first receiving area is formed along the longitudinal direction by two respective, mutually facing longitudinal walls, wherein at least one of the longitudinal walls runs at a slant to the bottom plane such that the first receiving area narrows from the top end toward the bottom.

2. The incubation trough according to claim 1, wherein the test strip when received in the first receiving area is facing by its back side toward the bottom and its front side is coated with at least one analytical reagent.

3. The incubation trough according to claim 1, wherein the bottom has a continuously constant bottom height along the first receiving area and along the second receiving area.

4. The incubation trough according to claim 1, wherein both of the longitudinal walls are slanted to the bottom plane, so that the first receiving area has a cross section with a conical extent from the top end to the bottom plane.

5. The incubation trough according to claim 1, wherein the second receiving area has, in a transition from the second receiving area to the first receiving area, at least one curvature which narrows from the second receiving area to the first receiving area.

6. The incubation trough according to claim 1, wherein the width of the second receiving area at bottom height is at least 4.5 mm, and
wherein the width of the first receiving area at bottom height is less than 3 mm.

7. The incubation trough according to claim 1, wherein the first receiving area has a width of at least 6 mm at its top end.

8. The incubation trough according to claim 1, wherein the at least one longitudinal wall makes an angle of at least 7° with a normal to the surface of the bottom plane.

9. The incubation trough according to claim 1, wherein the transverse wall makes an angle in the range of 110° to 150° with the bottom of the second receiving area.

10. An incubation tray, comprising:
a plurality of incubation troughs according to claim 1.

11. The incubation tray according to claim 10, wherein said plurality of incubation troughs is arranged parallel to each other.

12. The incubation tray according to claim 10, wherein two of the parallel arranged incubation troughs each have a respective centre axis in the longitudinal direction,
wherein the respective centre axes have a spacing from each other in the range of 8.5 mm to 9.5 mm.

13. A system, comprising:
an incubation trough according to claim 1, and
at least one test strip, which is coated on at least one side with at least one analytical reagent.

14. A method for the detection of biological material, comprising:
contacting the system according to claim 13 with a sample comprising said biological material.

* * * * *